United States Patent [19]

Sponer et al.

[11] Patent Number: 5,037,828

[45] Date of Patent: Aug. 6, 1991

[54] PIPERAZINE DERIVATIVES, USES THEREOF AND PHARMACEUTICAL COMPOSITIONS CONTING THEM

[75] Inventors: Gisbert Sponer, Laudenbach; Harald D. Borbe-Volmer, Maniz; Jürgen Engel, Alzenau; Bernhard Kutscher, Maintal; Georg Niebch, Rodenbach; Marianne Siebert-Weigel, Frankfurt, all of Fed. Rep. of Germany

[73] Assignee: Boehringer Mannheim GmbH, Mannheim, Fed. Rep. of Germany

[21] Appl. No.: 533,139

[22] Filed: Jun. 6, 1990

[30] Foreign Application Priority Data

Jun. 7, 1989 [DE] Fed. Rep. of Germany ....... 3918542

[51] Int. Cl.⁵ .................. A61K 31/495; C07D 296/08
[52] U.S. Cl. .................... 514/255; 544/392; 544/394
[58] Field of Search ................ 544/392, 394; 514/255

[56] References Cited

U.S. PATENT DOCUMENTS 3,997,666 12/1976 Witte et al. ................... 424/250
3,997,667 12/1976 Witte et al. ................... 514/255

FOREIGN PATENT DOCUMENTS 0089634 3/1983 European Pat. Off. .
2155697 6/1972 Fed. Rep. of Germany .
2235597 1/1974 Fed. Rep. of Germany .
2408804 9/1975 Fed. Rep. of Germany .

*Primary Examiner*—Cecilia Shen
*Attorney, Agent, or Firm*—Armstrong, Nikaido, Marmelstein, Kubovcik & Murray

[57] ABSTRACT

The present invention provides compounds of the general formula:

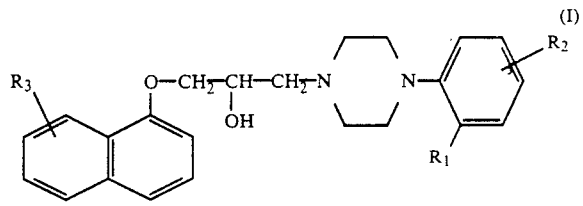

wherein $R_1$ is a hydroxyl group or a methoxy radical, $R_2$ is a hydrogen atom or a hyroxyl group and $R_3$ is a hydrogen atom or a hydroxyl group, with the proviso that $R_2$ and $R_3$ are not simultaneously hydrogen atoms when $R_1$ is a methoxy radical; and the pharmacologically acceptable salts thereof.

The present invention also provides processes for the preparation of these compounds and pharmaceutical compositions containing them.

10 Claims, No Drawings

PIPERAZINE DERIVATIVES, USES THEREOF AND PHARMACEUTICAL COMPOSITIONS CONTING THEM

The present invention is concerned with new derivatives of piperazine, processes for the preparation thereof and pharmaceutical compositions containing them.

The new derivatives of piperazine according to the present invention are hydroxylated 1-phenyl-4-[3-naphth-1-yloxy)-2-hydroxypropyl]-piperazines of the general formula:

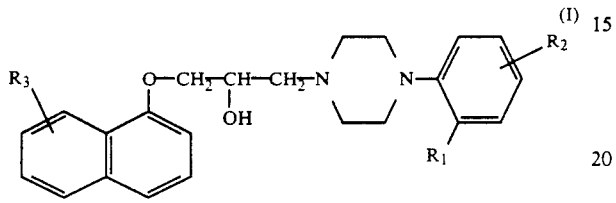

wherein $R_1$ is a hydroxyl group or a methoxy radical, $R_2$ is a hydrogen atom or a hydroxyl group and $R_3$ is a hydrogen atom or a hydroxyl group, with the proviso that $R_2$ and $R_3$ are not both hydrogen atoms when $R_1$ is a methoxy radical; and the pharmaceutically acceptable salts thereof.

From U.S. Pat. No. 3,997,666 is known the compound 1-(2-methoxyphenyl)-4-[3-(naphth-1-yloxy)-2-hydroxypropyl]-piperazine which possesses antihypertensive properties and inhibits anaphylactoid reactions in rats induced by dextran.

The new compounds according to the present invention also possess outstanding antihypertensive properties. In addition, they can be used for the therapy of dysuria in cases of prostatic hypertrophy. Therefore, they are valuable pharmaceuticals for the treatment of these diseases.

Preferred compounds of general formula (I) include:

1-(2-methoxy-4-hydroxyphenyl)-4-[3-(naphth-1-yloxy)-2-hydroxypropyl]-piperazine,
1-(2-methoxyphenyl)-4-[3-(4-hydroxynaphth-1-yloxy)-2-hydroxypropyl]-piperazine and
1-(2-hydroxyphenyl)-4-[3-(naphth-1-yloxy)-2-hydroxypropyl]-piperazine.

The substituent $R_3$ can be in any of the positions of the naphthyl ring but is preferably in the 4-position.

The compounds according to the present invention can be prepared in known manner, for example as follows:

a) a compound of the general formula:

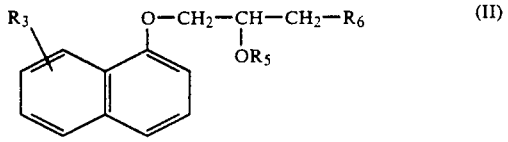

in which $R_3$ is a hydrogen atom or an optionally protected hydroxyl group, $R_5$ is a hydrogen atom and $R_6$ is a halogen atom or $R_5$ and $R_6$ can together represent a valency bond, is reacted with a compound of the general formula:

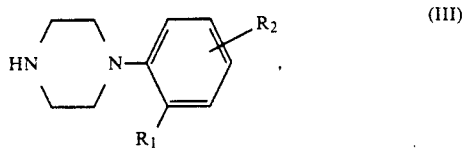

in which $R_1$ and $R_2$ have the above-given meanings; or
b) a compound of the general formula:

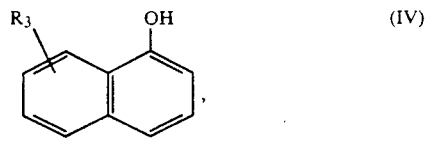

in which $R_3$ is a hydrogen atom or an optionally protected hydroxyl group, is reacted with a compound of the general formula:

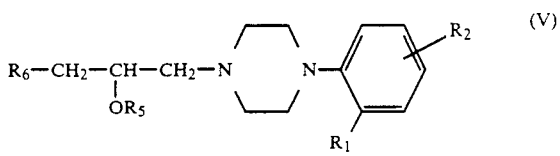

in which $R_1$ and $R_2$ have the above-given meanings, $R_5$ is a hydrogen atom and $R_6$ is a halogen atom or $R_5$ and $R_6$ can together represent a valency bond; and subsequently the hydroxyl protective group is optionally split off and the compound thus obtained is, if desired, converted into a pharmacologically acceptable salt.

When $R_6$ is a halogen atom, this is preferably a chlorine atom.

The hydroxyl protective group is preferably a benzyl radical.

The reactions are preferably carried out by mixing equimolar amounts of the reaction components with the addition of a solvent, for example methanol, ethanol or isopropanol, followed by heating under reflux.

The starting compounds of general formula (II) can be obtained by reacting 1-naphthol derivatives with epichlorohydrin, whereby, in the case of dihydroxy derivatives, the second hydroxyl group is protected by a benzyl radical which, after the reaction with a compound of general formula (III), is split off in the usual way, for example by hydrogenation in the presence of palladium/charcoal.

The compounds of general formula (V) are obtained in an analogous manner by reacting known corresponding N-phenylpiperazines with epichlorohydrin. The further reaction with 1-naphthol derivatives again takes place in the presence of an alcohol under reflux.

For the preparation of salts, the compounds according to the present invention are reacted with pharmacologically acceptable organic or inorganic acids, for example hydrochloric acid, sulphuric acid, phosphoric acid, lactic acid, citric acid or an alkylsulphonic acid.

For the preparation of pharmaceutical compositions, the compounds according to the present invention or the salts thereof are mixed in the usual way with appropriate pharmaceutical carrier materials, aroma, flavouring and colouring materials and formed, for example, into tablets or dragees or, with the addition of appropriate adjuvants, suspended or dissolved in water or an oil, for example olive oil.

The dosage of the compounds according to the present invention depends upon the nature of the disease, as well as upon the age of the patient. In the case of oral therapy, there are usually administered amounts of active material of from 10 to 100 mg. 1 to 3 times a day.

The following Examples are given for the purpose of illustrating the present invention:

EXAMPLE 1

1-(2-hydroxyphenyl)-4-[3-(naphth-1-yloxy)-2-hydroxypropyl]-piperazine 4.56 g. (0.025 mole) 1-(2-hydroxyphenyl)-piperazine and 5.6 g. (0.028 mole) 2,3-epoxypropyl naphthyl ether are dissolved in 50 ml. isopropanol and the solution obtained is heated under reflux for 5 hours, while stirring. Thereafter, the reaction mixture is diluted with a further 50 ml. isopropanol and acidified isopropanolic hydrochloric acid. A voluminous product precipitates out which is filtered off with suction, washed several times with isopropanol and recrystallised from methanol. Yield 8.8 g. (77% of theory); m.p. 249°–250° C.

EXAMPLE 2

1-(2-Methoxy-4-hydroxyphenyl)-4-[3-(naphth-1-yloxy)-2-hydroxypropyl]-piperazine

A solution of 4.16 g. (0.02 mole) 1-(2-methoxy-4-hydroxyphenyl)-piperazine and 4.2 g. (0.021 mole) 2,3-epoxypropyl naphthyl ether in 50 ml. isopropanol is heated under reflux for 4 hours, while stirring. The solution is evaporated and the tarry residue obtained is dissolved in methanol. It is acidified with isopropanolic hydrochloric acid and diethyl ether carefully added thereto, an oily product precipitating out which is separated by decanting off. The solution is diluted with acetone. After a short time, the compound begins to crystallise out. When crystallisation is complete, the crystals are filtered off with suction and again recrystallised from methanol/diethyl either. Yield 4.8 g. (50% of theory); m.p. 230°–232° C.

EXAMPLE 3

1-(2-Methoxyphenyl)-4-[3-(4-hydroxynaphth-1-yloxy)-2-hydroxypropyl]-piperazine a) 1-Benzyloxy-4-hydroxynaphthalene 23.7 g. (0.147 mole) 1,4-Dihydroxynaphthalene (purified by shaking an ethereal solution thereof with sodium dithionite solution) are dissolved in 200 ml. acetone. After adding 20.3 g. (0.147 mole) of pulverised potassium hydroxide and heating to reflux temperature, 18.6 g. (16.9 ml.) benzyl chloride are added dropwise thereto in the course of 60 minutes. The reaction mixture is thereafter heated under reflux for 4 hours while stirring, evaporated and the residue is mixed with 100 ml. water and extracted with diethyl ether. The ethereal solution is dried with anhydrous magnesium sulphate, filtered and evaporated. The tar-like residue is extracted with cyclohexane. The combined extracts are cooled, considerable amounts of a tarry product thereby first separating out. Thereafter, the pure compound crystallises out. It is washed with cyclohexane and dried. Yield 4.3 g. (11.9% of theory); m.p. 118°–119° C.

b) 1-Benzyloxy-4-(2,3-epoxypropyl)-naphthyl ether

To a solution of 4.3 g. (0.017 mole) 1-hydroxy-4-benzyloxynaphthalene in 15 ml. (0.19 mole) epichlorohydrin, which is heated to its boiling point while stirring, is carefully added dropwise 3.7 ml. 5M aqueous sodium hydroxide solution (0.0187 mole). The apparatus used for carrying out the reaction is equipped with a water separator so that the water distils off azeotropically from the reaction mixture with epichlorohydrin. After distilling off the theoretical amount of water, the reaction mixture is further heated under reflux for 1 hour while stirring, thereafter mixed with 50 ml. toluene, filtered off from inorganic components and the solution evaporated on a rotary evaporator. The product obtained is used for the next reaction step without further purification. Yield 6.1 g.

c)

1-(2-Methoxyphenyl)-4-[3-(4-benzyloxynaphth-1-yloxy)-2-hydroxypropyl]-piperazine A solution of 5.2 g. (0.017 mole) 1-benzyloxy-4-(2,3-epoxypropyl) naphthyl ether and 8.3 g. (0.034 mole) 1-(2-methoxyphenyl)-piperazine in 50 ml. isopropanol is heated under reflux, while stirring, for about 5 hours with the addition of a small amount of water. Thereafter, the reaction mixture is evaporated and the oily residue is purified by column chromatography using silica gel (Geduran S, 60; elution agent: methylene dichloride/methanol/25% aqueous ammonia solution 90:10:1 v/v/v). After evaporation of the collected eluates, the residue obtained is dissolved in methanol, acidified with isopropanolic hydrochloric acid and mixed with diethyl ether until the commencement of turbidity. The product which crystallises out is filtered off with suction, washed with acetone and again recrystallised from methanol/diethyl ether. Yield 4.8 g. (56% of theory); m.p. 143°–145° C.

d)

1-(2-Methoxyphenyl)-4-[3-(4-hydroxynaphth-1-yloxy)-2-hydroxypropyl]-piperazine 2.8 g. (0.005 mole) of the benzyloxy compound obtained in c) are hydrogenated in 50 ml. methanol in the presence of palladium/charcoal (10%) at 45° to 50° C. and under a hydrogen pressure of a 60 cm. high water column. After about 2 hours, the take up of hydrogen is ended. The resulting compound is sparingly soluble so that it crystallises out of the solution already during its formation. About 150 ml. methanol are added thereto, the mixture is heated to the boil while stirring and the catalyst is removed by hot filtration. Thereafter, the filtrate obtained is substantially evaporated in a vacuum and the crystals obtained are filtered off with suction, washed with methanol and dried. Yield 2.3 g. (95% of theory); m.p. 225°–226° C.

PHARMACOLOGICAL TESTS RESULTS

The pharmacological activity of the compound of Example 3 and the known compound naftopidil (U.S. Pat. No. 3,997,666) were investigated in the following experiments:

1. The affinities of the compounds were studied in receptor binding studies using prazosin as tritium-labeled ligand. The investigations were performed in brain membrane homogenates. The affinity was expressed as $IC_{50}$-value (the $IC_{50}$-value is the concentration in nmol/l which displaces 50% of the labeled ligand). Low values indicate a high affinity.

2. In vitro investigations were performed on isolated rat aortic strips precontracted with noradrenaline ($10^{-5}$M). The test compounds were added to the bath solution at concentrations of $3 \times 10^{-6}$M in order to test for vasorelaxation. The relaxation was evaluated at the end of an incubation period of 25 min. High values indicate a strong vasorelaxing effect.

3. The blood pressure lowering activity of the test compounds was investigated in conscious spontaneously hypertensive rats. The blood pressure response to the test compounds was evaluated by means of continuous monitoring of the mean arterial blood pressure via an implanted catheter, electromagnetic transducer and a direct recording system. The test compounds were injected at a dose of 10 mg/kg i.v. and the blood pressure response was determined 15 min after administration.

All the experiments consisted of 4–6 individual experiments, with the means of the results reported in the following table. The results demonstrate that the compound of the invention has a higher affinity to the $\alpha_1$-receptors, induces a more pronounced vasorelaxation and decreases the blood pressure more than the known compound naftopidil.

| compound | $\alpha_1$-receptor affinity $IC_{50}$ (nmol/l) | vasorelaxation $3 \times 10^{-6}$M (%) | blood pressure decrease 10 mg/kg i.v. (mmHg) |
|---|---|---|---|
| naftopidil | 235.0 | 53 | 31 |
| Example 3 | 52.7 | 85 | 48 | naftopidil = 1-(2-methoxyphenyl)-4-/3-(naphth-1-yloxy)-2-hydroxypropyl/-piperazine (U.S. Pat. No. 3,997,666)

We claim:

1. Compound of the formula:

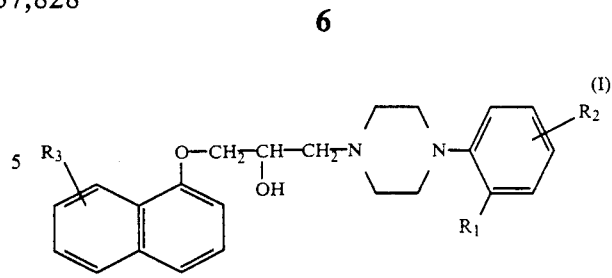

wherein
$R_1$ is a hydroxyl group or a methoxy radical,
$R_2$ is a hydrogen atom or a hydroxyl group, and
$R_3$ is a hydrogen atom or a hydroxyl group, provided that when $R_1$ is a methoxy radical, then at least one of $R_2$ and $R_3$ is a hydroxyl group;
or a pharmacologically acceptable salt thereof.

2. Compound of claim 1, wherein said compound is 1-(2-methoxy-4-hydroxyphenyl)-4-[3-(naphth-1-yloxy)-2-hydroxypropyl]-piperazine.

3. Compound of claim 1, wherein said compound is 1-(2-methoxyphenyl)-4-[3-(4-hydroxynaphth-1-yloxy-2-hydroxypropyl]-piperazine.

4. Compound of claim 1, wherein said compound is 1-(2-hydroxyphenyl)-4-[3-naphth-1-yloxy)-2-hydroxypropyl]-piperazine.

5. Composition for the treatment of hypertension or for the therapy of dysuria in cases of prostatic hypertrophy comprising a therapeutically effective amount of a compound of claim 1 and a pharmaceutically acceptable carrier.

6. Composition for the treatment of hypertension or of dysuria due to prostatic hypertrophy comprising a therapeutically effective amount of a compound of claim 3 and a pharmaceutically acceptable carrier.

7. A method of treating hypertension in a patient in need of said treatment or of the therapy of dysuria in cases of prostatic hypertrophy in a patient in need of said therapy, said method comprising administering to said patient an antihypertensive-effective amount or a dysuria therapy-effective amount of a compound of claim 1.

8. Method of claim 7, wherein said amount is from 10 to 100 mg. 1 to 3 times a day.

9. A method of treating hypertension or of treating dysuria due to prostatic hypertrophy in a patient in need of said treatment, said method administration an effective amount of a compound of claim 3.

10. Method of claim 9, wherein said amount is from 10 to 100 mg. 1 to 3 times a day.

* * * * *

UNITED STATES PATENT AND TRADEMARK OFFICE
CERTIFICATE OF CORRECTION

PATENT NO. : 5,037,828

DATED : August 6, 1991

INVENTOR(S) : Gisbert SPONER et al.

It is certified that error appears in the above-identified patent and that said Letters Patent is hereby corrected as shown below:

On the title page, item [54] and in column 1, lines 1-3, the title "PIPERAZINE DERIVATIVES, USES THEREOF AND PHARMACEUTICAL COMPOSITIONS CONTING THEM" should read -- PIPERAZINE DERIVATIVES, USES THEREOF AND PHARMACEUTICAL COMPOSITIONS CONTAINING THEM --.

Signed and Sealed this

Second Day of February, 1993

Attest:

STEPHEN G. KUNIN

Attesting Officer

Acting Commissioner of Patents and Trademarks